(12) United States Patent
Nissilä et al.

(10) Patent No.: US 6,443,905 B1
(45) Date of Patent: Sep. 3, 2002

(54) METHOD AND ARRANGEMENT FOR BLOOD PRESSURE MEASUREMENT

(75) Inventors: Seppo Nissilä; Eija Vieri-Gashi, both of Oulu; Mika Sorvisto, Ylivieska; Mika Niemimäki, Oulu, all of (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/508,354

(22) PCT Filed: Sep. 14, 1998

(86) PCT No.: PCT/FI98/00720
§ 371 (c)(1),
(2), (4) Date: Mar. 9, 2000

(87) PCT Pub. No.: WO99/13769
PCT Pub. Date: Mar. 25, 1999

(30) Foreign Application Priority Data

Sep. 12, 1997 (FI) .................................................. 973680

(51) Int. Cl.⁷ .................................................. A61B 5/02
(52) U.S. Cl. ...................................... 600/490; 600/500
(58) Field of Search .............................. 600/481, 485, 600/490, 491, 492, 493, 494, 495, 496, 500, 501, 502, 503

(56) References Cited

U.S. PATENT DOCUMENTS

| 4,117,835 A | 10/1978 | Williams |
| 4,796,184 A | 1/1989 | Bahr et al. |
| 5,033,471 A | 7/1991 | Yokoe et al. |
| 5,267,567 A | 12/1993 | Aung et al. |
| 5,279,303 A | 1/1994 | Kawamura et al. |
| 5,752,920 A | 5/1998 | Ogura et al. |
| 5,865,756 A | * 2/1999 | Peel, III ..................... 600/490 |

FOREIGN PATENT DOCUMENTS

| DE | 26 05 528 A1 | 8/1977 |
| EP | 0 651 969 A3 | 5/1995 |
| WO | WO 97/03606 | 2/1997 |

* cited by examiner

*Primary Examiner*—Kevin Shaver
*Assistant Examiner*—Navin Natnithithadha
(74) *Attorney, Agent, or Firm*—Hoffmann & Baron, LLP (57) ABSTRACT

The invention relates to a method and arrangement for blood pressure measurement. In the method, a variable compressive acting pressure is applied to a measuring point, such as a person's extremity at a compression point by a pressure generator, and at the same time the effect of the variable pressure on the artery is measured at a second point, the second point being located farther away from the heart, i.e. closer to the end point of peripheral circulation than the compression point to which the pressure is applied. In the method diastolic pressure (PDIAS) and/or systolic pressure (PSYS) is determined as a result of an actual measurement. In addition, the method further includes an estimation cycle for the actual measurement, during which the magnitude of the pressure pulse is measured by a sensor measuring a pressure pulse signal, and in the estimation one or more statistical parameters are calculated from the pressure pulse measurement data to represent the magnitude of pressure pulse variation for forecasting and/or depicting the quality of the actual blood pressure measurement.

53 Claims, 8 Drawing Sheets

METHOD AND ARRANGEMENT FOR BLOOD PRESSURE MEASUREMENT

BACKGROUND OF THE INVENTION

1. Field of the Invention

The invention relates to a method for blood pressure measurement, in which method a variable compressive acting pressure is applied to a measuring point, such as a person's extremity or the like, at a compression point by a pressure generator, and at the same time the effect of the variable pressure on the artery is measured at a second point, the second point being located farther away from the heart, i.e. closer to the end point of peripheral circulation than the compression point to which the pressure is applied, and in which method diastolic pressure and/or systolic pressure is determined to determine the measurement result of an actual blood pressure measurement.

A second embodiment of the invention relates to a method for blood pressure measurement, in which method a variable compressive acting pressure is applied to a measuring point, such as a person's extremity or the like, at a compression point by a pressure generator, and in which method diastolic pressure and/or systolic pressure is determined oscillometrically to determine the measurement result of an actual blood pressure measurement by measuring a pressure oscillation signal which is measurable from the pressure generator.

The invention also relates to an arrangement for blood pressure measurement, comprising a pressure generator for applying an acting pressure to a measuring point, such as a person's extremity or the like, the arrangement comprising a measuring element for measuring the acting pressure, the arrangement further comprising an interpreting unit for determining systolic pressure and/or diastolic pressure, the arrangement comprising a sensor for simultaneous measurement of the effect of the variable pressure on an artery at a second point, said second point being farther away from the heart, i.e. closer to the end point of peripheral circulation, than the compression point to which the acting pressure is applied.

The second embodiment of the invention relates to an arrangement for blood pressure measurement, comprising a pressure generator for applying an acting pressure to a measuring point, such as a person's extremity or the like, the arrangement comprising a measuring element for measuring the acting pressure and its effect by measuring a pressure oscillation signal of the pressure generator, the arrangement further comprising an interpreting unit for determining systolic pressure and/or diastolic pressure oscillometrically from the pressure oscillation signal.

2. Brief Description of the Related Art

The heart pumps and causes blood to flow in the blood vessels, arteries and veins. The pumping produces pressure in the blood, i.e. blood pressure. Blood pressure is particularly affected by heartbeat and the resistance provided by peripheral circulation. Psychic factors, medication, smoking and other factors, such as a person's state, i.e. whether a person is asleep or awake, are also important.

The terms systolic pressure, diastolic pressure and venous pressure, are used when discussing blood pressure.

Technically, from the point of view of measurement, systolic pressure refers to the pressure at which an artery becomes blocked, i.e. heartbeat stops. Physiologically, systolic pressure refers to the maximum pressure generated by a pumping cycle of the heart.

Technically, from the point of view of measurement, diastolic pressure refers to the pressure at which heartbeat is resumed when the pressure pressing the artery is reduced. Physiologically, diastolic pressure refers to the minimum venous pressure value between two pumping cycles of the heart.

Venous pressure refers to the average pressure in a vein. At a certain stage of venous pressure measurement, a systolic and diastolic point can also be detected.

Blood pressure measurement is divided into two main categories: invasive, i.e. measurement from inside the body, and non-invasive, i.e. measurement from the outside of the body. The drawback in the invasive method is naturally that the measurement is made from inside a person's body by the use of e.g. a catheter placed in an artery. The invasive method and the equipment solutions involved are unpleasant for a person, and the measurements involve much work and are cumbersome, since they require operating theatre conditions. A special drawback is the risk of infection and bleeding of the artery.

Currently two methods are known for non-invasive blood pressure measurement, i.e. measurement from outside of the body. These include the auscultatory measurement and the oscillometric measurement. The auscultatory method utilizes a stethoscope and an occluding cuff provided with a mercury manometer and a pressure pump, the cuff encircling a person's extremity, such as the arm. The auscultatory method is based on auscultation of sounds known as the Korotkoff sounds by the stethoscope. The Korotkoff sounds are created by blood flowing in a partially occluded artery. In the auscultatory method the pressure of the occluding cuff, i.e. the acting pressure, is first raised above the estimated systolic pressure, whereby blood flow in the extremity being measured, such as the arm, is occluded. The pressure of the occluding cuff is then allowed to decline gradually, while the stethoscope is placed over the artery for auscultation on the distal side with respect to the occluding cuff. Once the pressure has been lowered sufficiently, snapping Korotkoff sounds can be detected by the stethoscope, and the current pressure is interpreted as the systolic pressure. Once the pressure of the occluding cuff is allowed to decline further, Korotkoff sounds are no longer heard, which means that the current pressure is the diastolic pressure at which the occluding cuff no longer occludes the artery. The drawback of the auscultatory method is its inaccuracy and that it requires an intent and experienced user.

Publication DE-2605528 teaches an application of the auscultatory method which additionally utilizes an optic pulse sensor disposed on the finger for following the variations in the pressure pulse. If the pressure pulse measured by the optic pulse sensor is observed to vary, this indicates a change in blood pressure from the previous measurement, and requires a new measurement. However, said procedure does not allow, recognize or suggest improvement of accuracy and reliability, only that said information indicates the need for a repeat measurement.

Furthermore, a manual method based on palpation is known, in which pressure is produced by an occluding cuff in the arm, and a finger is used to palpate the pressure pulse of the radial artery, i.e. heartbeat. However, said method is inaccurate and unreliable.

Another widely used non-invasive method is the oscillometric measurement, in which an occluding cuff and the same principle are used, i.e. the acting pressure is first raised high, i.e. over the estimated systolic pressure, and then slowly declined, during which a pressure sensor comprised by the cuff is used to follow or observe the pressure oscillation signal of the cuff. Thus the essential difference as compared with the auscultatory method is that in the oscillometric method an electronic monitoring unit comprised by the device is used to follow the pressure oscillation measured by the pressure sensor inside the cuff instead of auscultation of an artery. As cuff pressure falls, the amplitude of the pressure oscillation in the cuff, i.e. the AC signal of the cuff pressure, increases to a certain pressure as the pressure is lowered, whereupon the oscillation decreases. When the pressure falls, oscillation, i.e. an AC-form pressure oscillation signal, or amplitude variation, is detectable in the cuff pressure. The amplitude of the pressure oscillation signal oscillation measured by the pressure sensor from the cuff reaches its maximum at a pressure known as mean arterial pressure. Systolic pressure can be measured relatively well by the oscillometric method, but diastolic pressure has to be calculated indirectly since the pressure oscillation signal oscillation measured by the cuff pressure sensor is still present at diastolic pressure, and hence indirect determination is used, in which the value of the diastolic pressure is the mean arterial pressure minus half of the difference between systolic and mean arterial pressure. A weakness of the oscillometric method is its inaccuracy and the resulting unreliability. Oscillometric devices and methods are technically simple, but this in turn results in the inability to monitor and observe the measurement and its reliability. The accuracy and reliability of oscillometric measurement have been improved by different signal processing methods by identifying different characteristics of the AC signal of the pressure pulse during measurement in association with determination of systolic and diastolic pressure. Publication U.S. Pat. No. 4,117,835, for example, discloses a method of monitoring the change in the AC signal derivative. However, in clinical measurements said methods have not been found to affect the accuracy.

A tonometric method, originally designed for ocular pressure measurement, has also been applied to blood pressure measurement. In the methods according to publication U.S. Pat. No. 5,033,471, the radial artery extending near a radius of the wrist is pressed. Since the surface resting against the sensor is even, intravenous pressure can be read at the middle sensor element. The method thus involves a direct non-invasive measurement. In principle the measurement is ideal and practical, but the skin causes a problem since it does not provide an ideal membrane between the sensor and the blood vessel. This is why calibration is required in tonometric methods, as described in e.g. publication U.S. Pat. No. 5279303.

Known methods and measurement arrangements provide no reliable way to estimate measurement quality, or reliability.

A common problem in non-invasive blood pressure meters is inaccuracy. Part of the inaccuracy is the result of physiological factors, such as normal blood pressure variation and change, even during measurement. Additional inaccuracy is caused by the inaccuracy of the measurement method and the meter. Measurement error can be as high as 10 mm Hg, but known meters do not allow the user to estimate the accuracy of the systolic and/or diastolic pressure reading. Often the user imagines that the accuracy of the last meter number, i.e. 1 mm Hg, is the accuracy of the meter, although in reality the inaccuracy may be as much as ±5 or ±10 mm Hg.

SUMMARY OF THE INVENTION

It is an object of the present invention to provide a new kind of method and arrangement for blood pressure measurement, avoiding the problems of known solutions.

The object is achieved by a method according to a first embodiment of the invention, characterized in that in addition to the actual blood pressure measurement, the method comprises an estimation cycle for the actual measurement, during which the magnitude of the pressure pulse is measured by a sensor measuring a pressure pulse signal, and that in the estimation one or more statistical parameters are calculated from the pressure pulse measurement data to represent the magnitude of pressure pulse variation for forecasting and/or depicting the quality of the actual blood pressure measurement.

The object is also achieved by a method according to a second embodiment of the invention, characterized in that in addition to the actual blood pressure measurement, the method comprises an estimation cycle for the actual measurement, during which the magnitude of the pressure oscillation signal is measured by a sensor measuring the pressure oscillation signal, and that in the estimation one or more statistical parameters are calculated from the pressure oscillation signal measurement data to represent the magnitude of pressure oscillation signal variation for forecasting and/or depicting the quality of the actual blood pressure measurement.

In the first embodiment, the measurement arrangement of the invention is characterized in that it comprises an estimation means for estimating the quality of an actual blood pressure measurement, and that the estimation means is in connection with the sensor measuring the pressure pulse at the measuring point and feeding the measurement data to the estimation means, the sensor being either the same sensor that is used in the actual blood pressure measurement for measuring the effect of the acting pressure, or a second, different sensor, and that the estimation means comprises a calculation means, adapted to calculate from the measurement data measured by the pressure pulse sensor one or more statistical parameters representing the magnitude of pressure pulse variation for forecasting and/or depicting the quality of the actual blood pressure measurement.

In the second embodiment, the measurement arrangement of the invention is characterized in that it comprises an estimation means for estimating the quality of an actual blood pressure measurement, and that the estimation means is in connection with the measuring element or with another sensor measuring the pressure oscillation signal and feeding the measurement data to the estimation means, and that the estimation means comprises a calculation means, adapted to calculate from the measurement data of the measured pressure oscillation signal one or more statistical parameters representing the magnitude of pressure oscillation signal variation for forecasting and/or depicting the quality of the actual blood pressure measurement.

The method and measurement arrangement of the invention are based on the idea that the actual blood pressure measurement is estimated on the basis of a pressure pulse measurement or a pressure oscillation signal measurement made before and/or after the actual blood pressure measurement.

The solution of the invention provides several advantages. By means of the invention, the user or nursing staff receive valuable additional information on the accuracy and representativeness of the result of the blood pressure measurement. Measurements of diastolic and systolic pressure are discrete measurements, and the invention allows the practicability of such a discrete measurement to be improved. The invention allows the rejection of measurement results the estimation result of which, calculated in the manner according to the invention, is too weak, and, on the other hand, allows the acceptance of measurement results with sufficiently good estimation results.

More reliable measurement results allow the right conclusions to be drawn from a person's real blood pressure values. Technically, the measurement arrangement of the invention can be implemented within a small space, if desired, e.g. as a wristband. Some parts of the measurement arrangement of the invention, such as the pressure pulse meter or the interpreting unit, can be applied to actual blood pressure measurements, if desired, in addition to the estimation of measurement quality.

The present invention is particularly well suitable for a novel palpation method which utilizes a sensor measuring arterial pressure pulse, but the invention can also be applied to oscillometric applications, in which measurements are carried out by a pressure cuff.

BRIEF DESCRIPTION OF THE DRAWINGS

In the following the invention will be described in greater detail with reference to the attached drawings, in which.

DETAILED DESCRIPTION OF THE INVENTION

The invention relates to a method and an arrangement for blood pressure measurement. The measurement arrangement will be described first.

The measurement arrangement comprises a cuff-like or other type of pressure generator 1, for applying pressure to a measuring point 3, such as a person's extremity 3 or the like, at a compression point A. The cuff-type pressure generator 1 obtains its pressure from a pressure source 1a, comprised by the arrangement, via a pressure line 1b. The pressure source 1a can be e.g. a pump.

The pressure serves to occlude the artery in the extremity 3 upon pressing and to open the artery when the pressure is released. The arrangement further comprises an element 5 for measuring the magnitude of the pressure generated by the pressure generator 1 for applying the pressure to the compression point A. The measuring element 5 can be e.g. a Si pressure sensor or other DC pressure sensor. The arrangement further comprises a sensor 7 for simultaneously measuring the effect of the variable acting pressure on an artery at a second point B. The sensor 7 can be e.g. a PVDF sensor (PolyVinyDiFluoride) or an EMF sensor (Electro Mechanical Film). Said second point B is a point which is farther away from the heart, i.e. closer to the end point of peripheral circulation than the compression point A, to which the pressure is applied. The measuring point B is thus at the distal, i.e. peripheral, side of the circulation. The measurement arrangement further comprises an interpreting means 9 for determining systolic and/or diastolic pressure.

Figure 1:
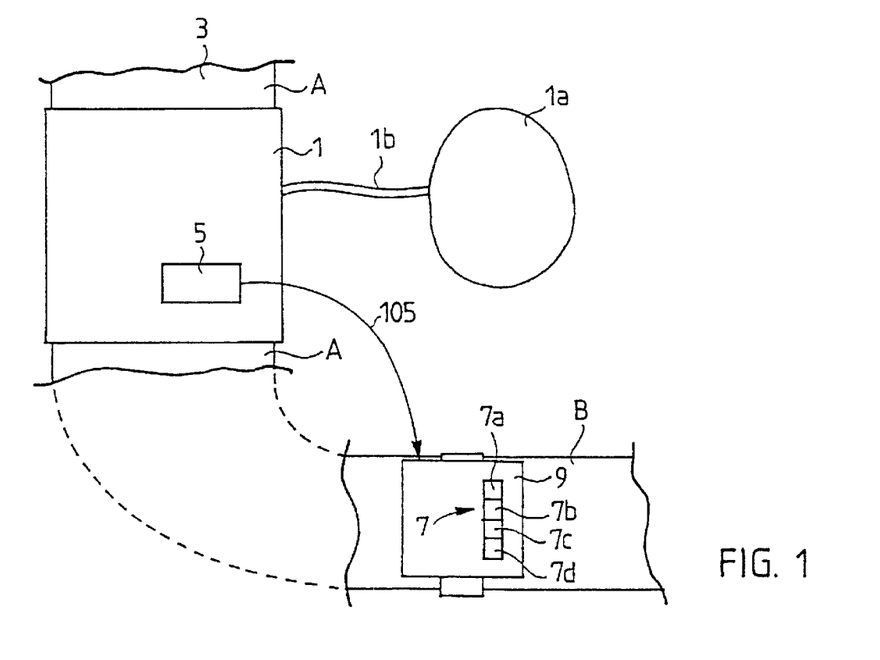
FIG. 1 shows a first embodiment of the measurement arrangement.
Figure 3:
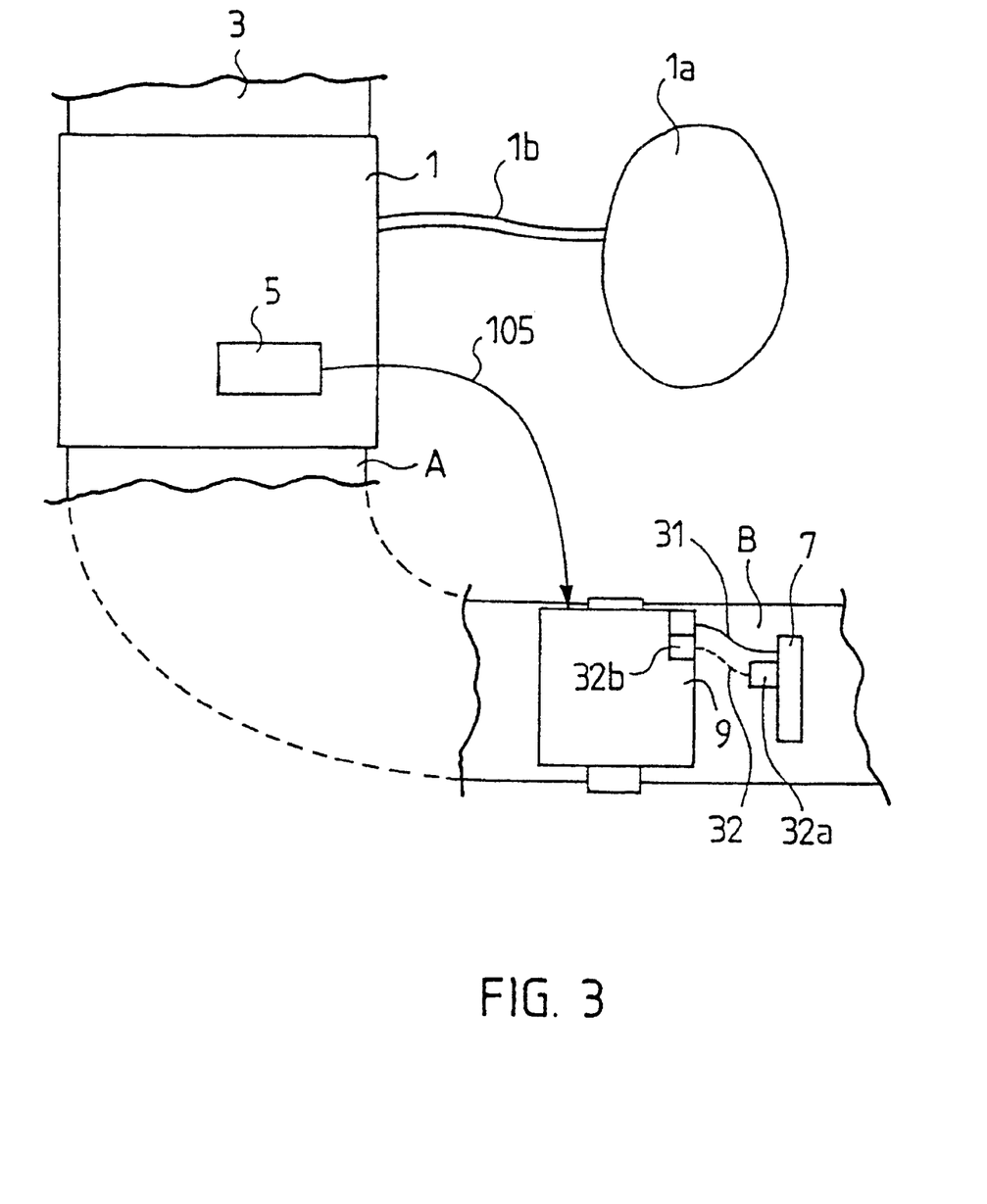
FIG. 3 shows a third embodiment of the measurement arrangement.

Said sensor 7 measures at the second point B the pressure pulse caused by heartbeat and is preferably separate from the pressure generator. The sensor 7 is coupled to said interpreting unit 9, to which a measuring signal, which is obtained from the measuring element 5 and depicts the measurement value of the acting pressure, is also coupled. Except for FIG. 9, the pressure pulse is preferably measured by a sensor 7 which, at least from the point of view of the technical operation of the measurement, is separate from the pressure generator, i.e. the sensor 7 measures the pressure pulse, i.e. the effect of the acting pressure, independently, not from the same signal source as the measuring element 5 measuring the acting pressure. FIGS. 1 and 3 arrow 105 shows in a simplified manner how the acting pressure is transferred from the measuring element 5 to the interpreting unit 9.

In some embodiments the sensor 7 can be in connection with the pressure generator or parts in connection therewith by e.g. a rod or conductor or otherwise, but in this case the pressure generator must be of a type which does not interfere with the operation of the sensor.

Figure 4:
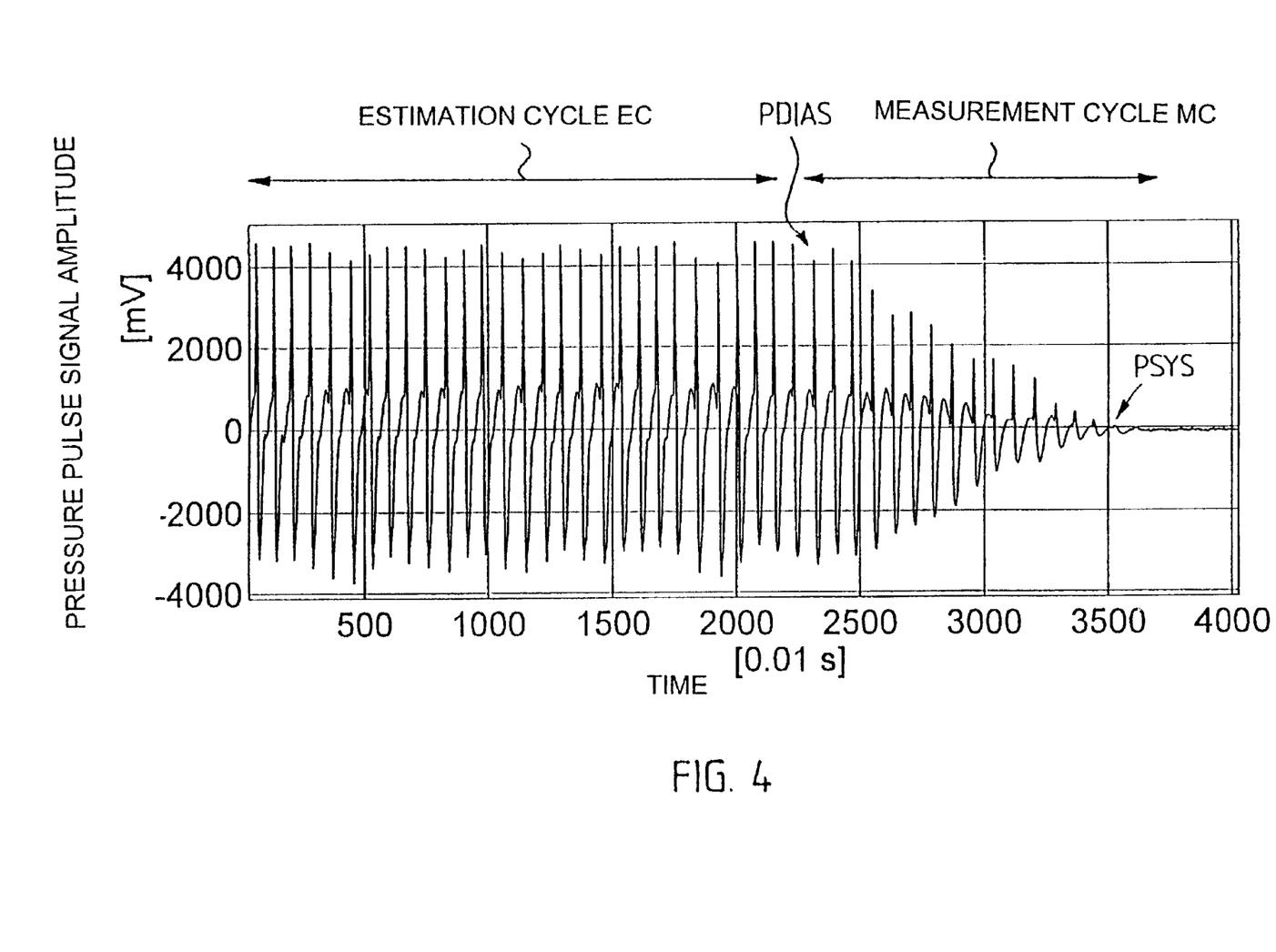
FIG. 4 shows a pressure pulse signal in an embodiment having an estimation cycle before the actual blood pressure measurement.
Figure 5:
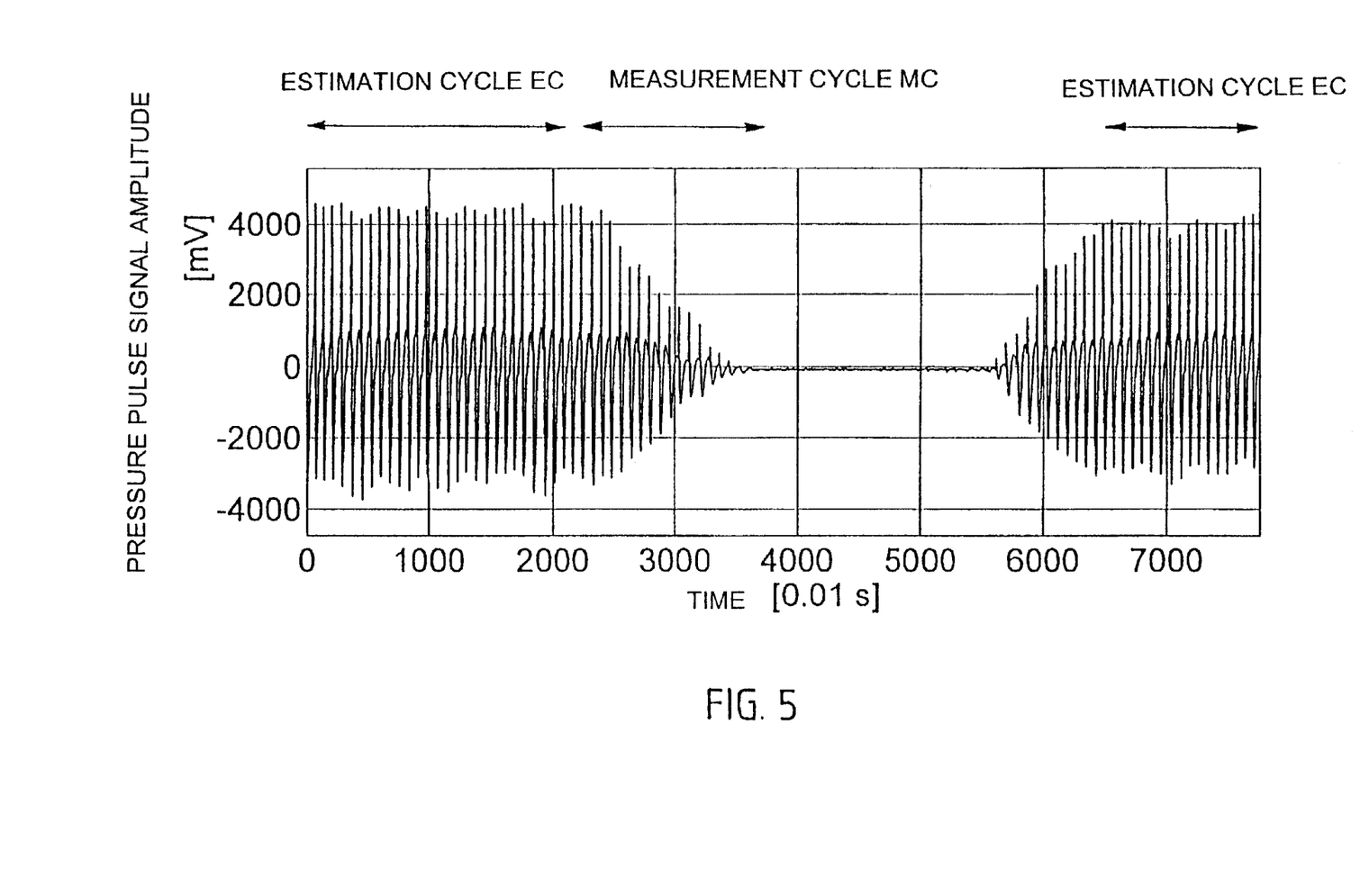
FIG. 5 shows a pressure pulse signal in an embodiment having an estimation cycle before and after the blood pressure measurement.

With reference to FIGS. 1 to 7, in the measurement arrangement, as far as actual blood pressure measurement, i.e. determination of systolic and/or diastolic pressure, is concerned, said interpreting unit 9 is arranged to determine diastolic pressure PDIAS and/or systolic pressure PSYS on the basis of a pressure which is acting upon the detection of a change, characteristic of diastolic pressure PDIAS and/or systolic pressure, in the pressure pulse signal measured by the sensor 7, which is preferably separate from the pressure generator and measures the artery (arterial pressure pulse), in the interpreting unit 9, more exactly in its interpreting element 9a. In FIGS. 4 and 5, reference MC shows the actual blood pressure measurement cycle. A measurement made during a falling acting pressure is involved, with the diastolic pressure PDIAS marked at a point of the pressure pulse signal where the amplitude starts to fall, and the systolic pressure PSYS at a point where the falling stops.

Figure 6:
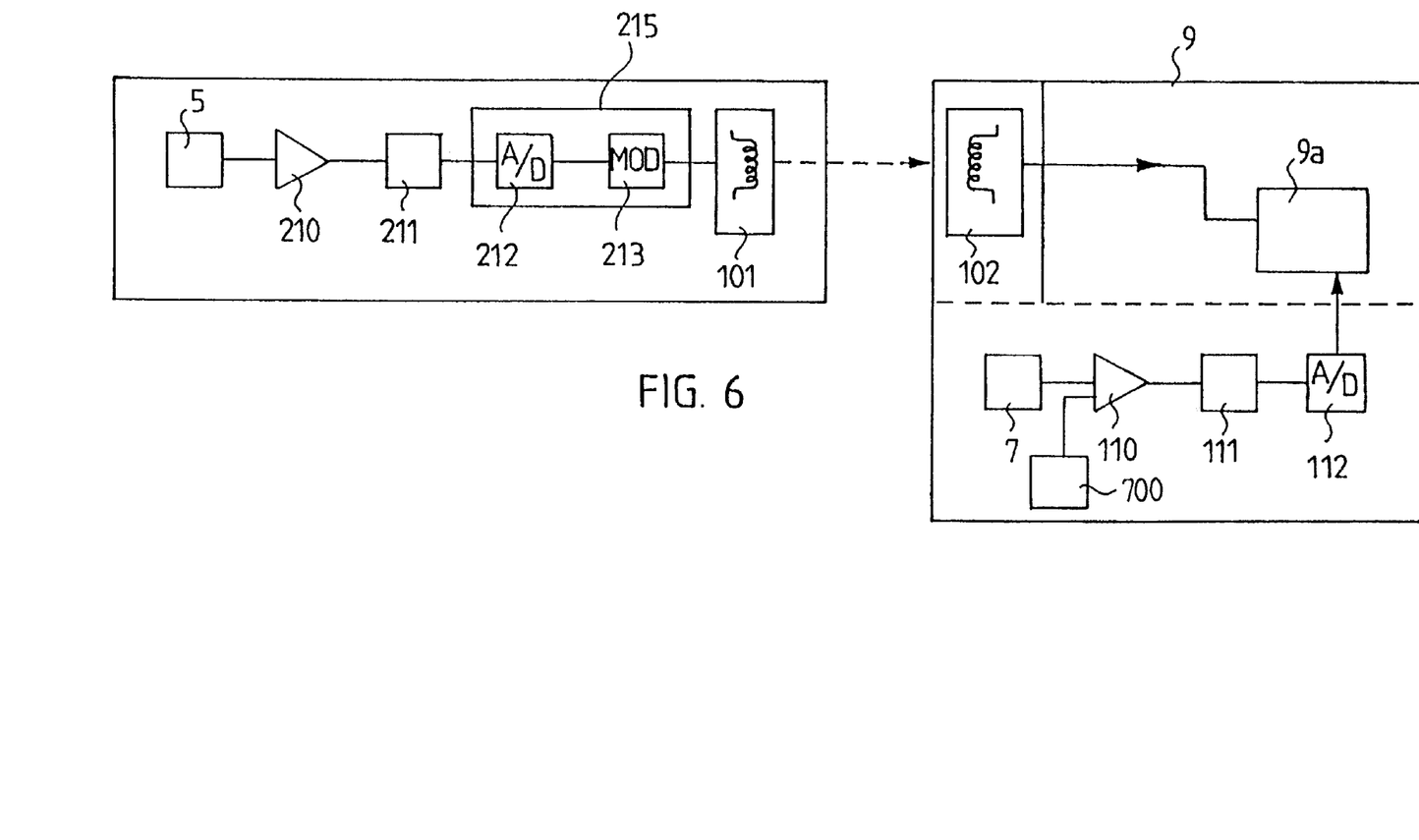
FIG. 6 shows an embodiment for transferring measurement data on the acting pressure and on the pressure pulse to the interpreting unit.

FIG. 6 shows an embodiment for transferring measurement data measured by the acting pressure measuring element 5 in connection with the pressure generator to the interpreting unit 9. FIG. 6 also shows an embodiment for processing the signal measured by the pressure pulse sensor 7 and for transferring it to the interpreting unit 9.

Referring to FIG. 6, a preferred embodiment of the invention involves a measurement arrangement comprising a wireless telemetric magnetic inductive coupling 101, 102 for transferring the measured acting pressure measuring signal from the measuring element 5 to the interpreting unit 9. Said coupling comprises a transmitter element 101, which obtains input data from the acting pressure measuring element 5, and a receiver element 102 in the interpreting unit 9. The transmitter element 101 comprises a coil 101a, to which the signal measured by the measuring element 5 is applied. The receiver element 102 comprises a second coil 102a. In the method the acting pressure measurement value is transferred to the interpreting unit 9 as a wireless telemetric transfer by means of the magnetic inductive coupling 101, 102 between the coils 101a, 102a. The connection 105 for transferring the signal measured by the acting pressure measuring element 5 to the interpreting unit 9, shown in FIGS. 1 and 3 in a simplified manner by arrow 105, can be a wired connection or wireless, as the transfer implemented by the inductive coupling by the components 101, 102 in FIGS. 2 and 6.

Referring to FIG. 6 and still to actual blood pressure measurement, in a preferred embodiment of the invention the measurement arrangement comprises an amplifier 210 and a filter 211 for filtering the acting pressure measuring signal obtained from the measuring element 5 to filter off an oscillating AC portion caused by the pulse. The measuring element 5 carries out a pressure/voltage conversion, for example, and in this case the amplifier 210 is a voltage amplifier. The filter 211, in turn, is a low-pass filter with an upper limit frequency of e.g. 1 to 5 Hz.

Referring to FIG. 6, in an embodiment mainly associated with actual blood pressure measurement, the arrangement further comprises an A/D converter 212 for A/D conversion of the filtered acting pressure signal. If an inductive coupling 101, 102 is used for transferring the signal measured by the acting pressure measuring element 5 to the interpreting unit 9, then the arrangement further comprises a modulator 213 or another signal modulator unit 213 for modulating the A/D converted signal e.g. to a frequency modulated signal or to another signal which can be applied to the transmitter unit 101 comprised by the inductive coupling. The signal modulator unit 213 can be e.g. a pulse width modulator or a frequency modulator. Together the blocks 212 and 213 form a signal modulator 215 which serves to modulate the signal into a transferable form for the transmitter element 101. It should be observed that the connection 101–102 could alternatively be optic. Said units 210 to 213 and 101 are most preferably part of the same entity as are the measuring unit 5 and the pressure generator 1.

However, the most essential idea of the present invention is not actual blood pressure measurement, but estimation of blood pressure measurement, i.e. estimation of measurement accuracy. The following will mainly deal with the estimation of actual blood pressure measurement.

The measurement arrangement of the invention is characterized in the it comprises an estimation means 960 for estimating the quality of the actual blood pressure measurement. The measurement arrangement is further characterized in that the estimation means 960 is in connection with a sensor which measures the pressure pulse from the measuring point for estimating the quality of the actual measurement and applies the measurement data to the estimation means, the sensor being either the same sensor 7 that is used in the actual blood pressure measurement to measure the effect of the acting pressure, or a second, different sensor 700. The measurement arrangement is further characterized in that the estimation means 960 comprises a calculation means 961, arranged to calculate from the measurement data measured by the pressure pulse measuring sensor 7 and/or 700 one or more statistical parameters representing the magnitude of pressure pulse variation for forecasting and/or depicting the quality of the actual blood pressure measurement.

Figure 8:
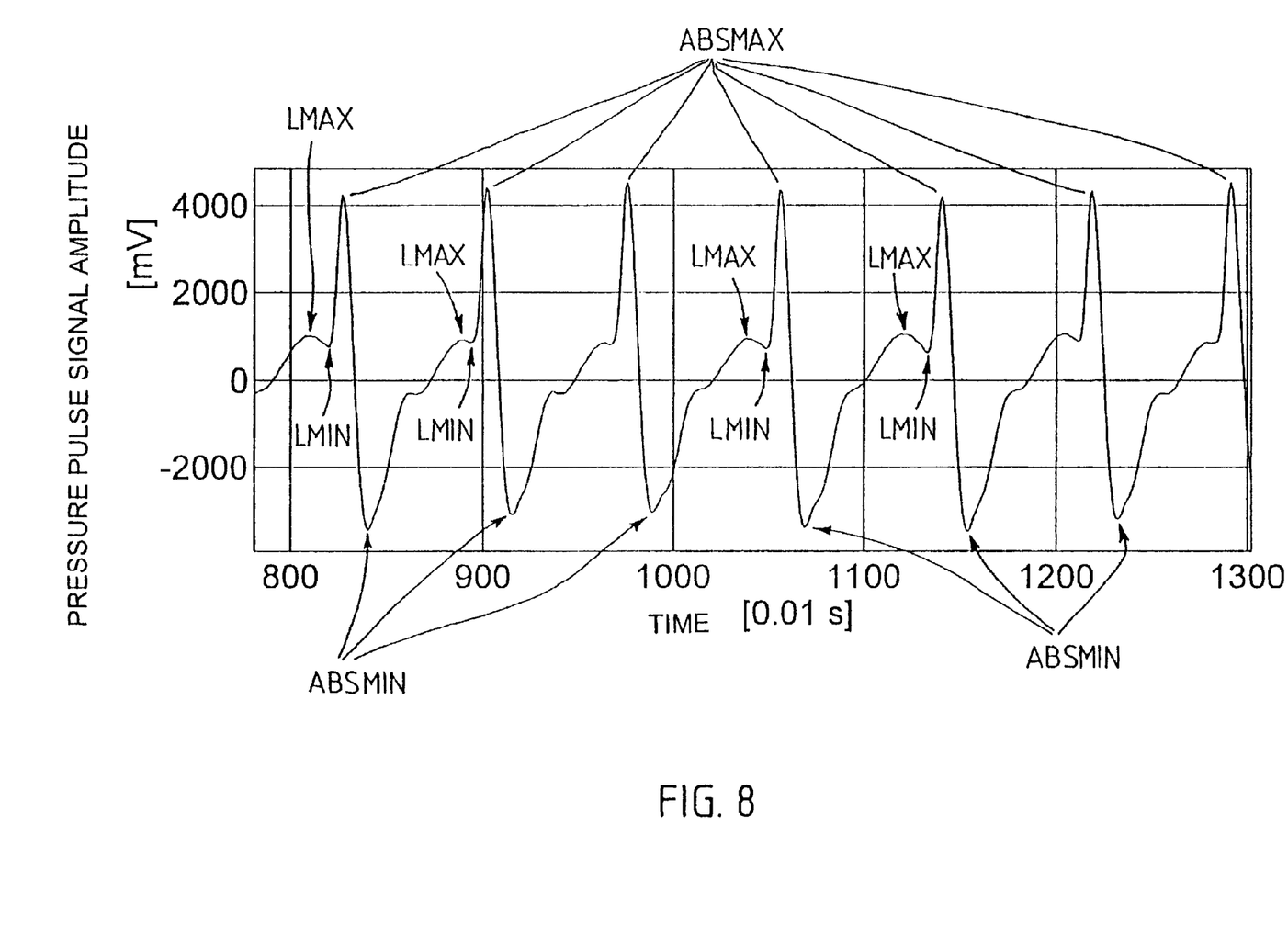
FIG. 8 shows a partial enlarged view of FIG. 4 for seven pressure sure pulses.

FIG. 8 shows a partial enlarged view of seven single pressure pulses of FIG. 4. For each pulse, FIG. 8 shows an absolute maximum ABSMAX, and absolute minimum ABSMIN, a local maximum LMAX and a local minimum LMIN. The difference between each absolute maximum and minimum represents the value of the amplitude.

The method and measurement arrangement of the invention preferably comprise arranging the calculation means 961 to calculate one or more of the following statistical parameters: maximum, minimum, magnitude of pressure pulse signal amplitude variation, standard deviation of pressure pulse signal amplitude variation, standard deviation and/or mean of the absolute maximums of the pressure pulse signal, standard deviation and/or mean of the absolute minimums of the pressure pulse signal, standard deviation and/or mean of the local maximums of the pressure pulse signal, standard deviation and/or mean of the local minimums of the pressure pulse signal. These parameters provide a representative estimate of measurement quality, i.e. measurement accuracy.

In the embodiments disclosed in the present application the pressure pulse is most preferably measured as an amplitude measurement, and naturally monitoring the magnitude of the pressure pulse is also based on monitoring amplitude values. However, instead of amplitude, the sensor 7 can measure pressure pulse frequency or phase, which also serve to indicate the magnitude of the pressure pulse, and hence, amplitude. The measurement may also involve amplitude measurement, amplitude data being converted into frequency or phase data. Thus the present invention is not only restricted to direct amplitude measurement and comparison by means of amplitude. This also holds true for pressure oscillation signal measurement by the measuring element 5 in FIG. 9.

In the method and measurement arrangement of a preferred embodiment of the invention, the sensor 7 (or 700), which measures the pressure pulse for blood pressure measurement estimation, is arranged to carry out the measurement before or after the actual blood pressure measurement, or both before and after the actual blood pressure measurement. FIG. 4 shows a pressure pulse signal measured for estimation in an embodiment in which the estimation measurement is carried out before the actual blood pressure measurement. In FIGS. 4 and 5 the estimation cycle is denoted by EC. FIG. 5, in turn, shows an embodiment involving an estimation cycle both before and after blood pressure measurement, i.e. having two estimation cycles EC. The applicant has found that the embodiment of FIG. 5 gives more reliable results, while calculation of the estimation result is faster by the version shown in FIG. 4.

Figure 7:
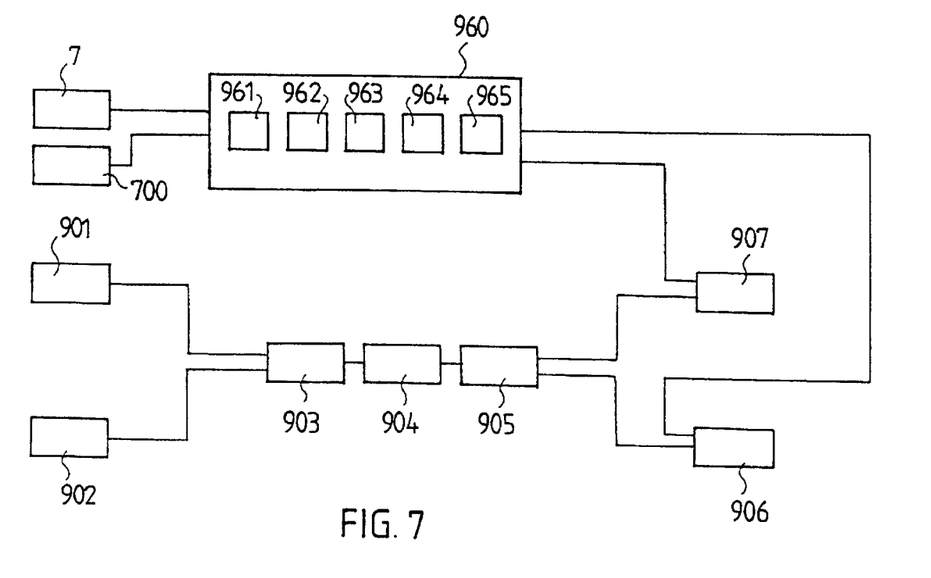
FIG. 7 shows the inner structure of the interpreting unit and the estimation means.

Referring to FIG. 7, in the method and measurement arrangement the estimation means preferably comprises a reference comparator 962, arranged to compare the result of the estimation with reference values set for the quality of the actual blood pressure measurement. Should the estimation result surpass the reference values set for the quality of the actual blood pressure measurement, the actual blood pressure measurement is initiated, controlled by the reference comparator 962, or the measurement result of a performed actual blood pressure measurement is accepted as the final result. Initiation of the actual measurement is feasible if an estimation carried out before the actual measurement is involved. Similarly, the result of an actual measurement could be accepted as the final result if an estimation carried out after the actual measurement is involved. Should the estimation result be worse than the reference values set for the quality of the actual blood pressure measurement, the actual blood pressure measurement is not initiated, or the result of a completed actual blood pressure measurement is rejected.

In the method and measurement arrangement of the invention the estimation means preferably comprises a trend indicator 963, arranged to estimate if the blood pressure value shows a trend towards a higher or lower value during estimation or if the trend is essentially indicative of a stable blood pressure value. The trend also serves to forecast or estimate measurement quality, i.e. measurement accuracy.

In a preferred embodiment of the invention the estimation means 960 to 965 are parts of the same entity as the interpreting unit 9, the estimation means 960 to 965 most preferably being part of the interpreting unit 9, as in FIG. 7.

Referring particularly to FIGS. 4, 5, 7, 8, and 10, in a preferred embodiment the estimation means 960 comprises a means 964 for observing the pressure pulse signal measurement in the estimation cycle EC and the pressure pulse signal measurement in the actual blood pressure measurement cycle MC as comparable measurements with regard to time. In said preferred embodiment the estimation means 960 comprises a determination means 965 for determining the point where the instant of determining the diastolic pressure PDIAS in the actual blood pressure measurement is located in relation to upper and lower peaks L and H of a pressure pulse signal variation signal S generated on the basis of the estimation cycle measurement and shown in FIG. 10. This provides a better estimate of the accuracy of diastolic pressure measurement.

To estimate the accuracy of systolic pressure measurement, a trend obtained from the estimation cycle EC measurement is employed. In this case, by using the means 964 and 965, the method observes the pressure pulse signal measurement of the estimation cycle EC and the pressure pulse signal measurement of the actual blood pressure measurement cycle MC as comparable measurements with respect to time, and the method determines the point where the instant of determining the systolic pressure PSYS of the actual blood pressure measurement is located in relation to upper and lower peaks (H and L) of a pressure pulse signal variation signal S estimated on the basis of the estimation cycle measurement EC.

The estimation cycle measurement and the actual blood pressure measurement are comparable measurements with respect to time, since both are measured as a function of time and as successive measurements on the same time axis, as can be seen from FIGS. 4 and 5.

Figure 10:
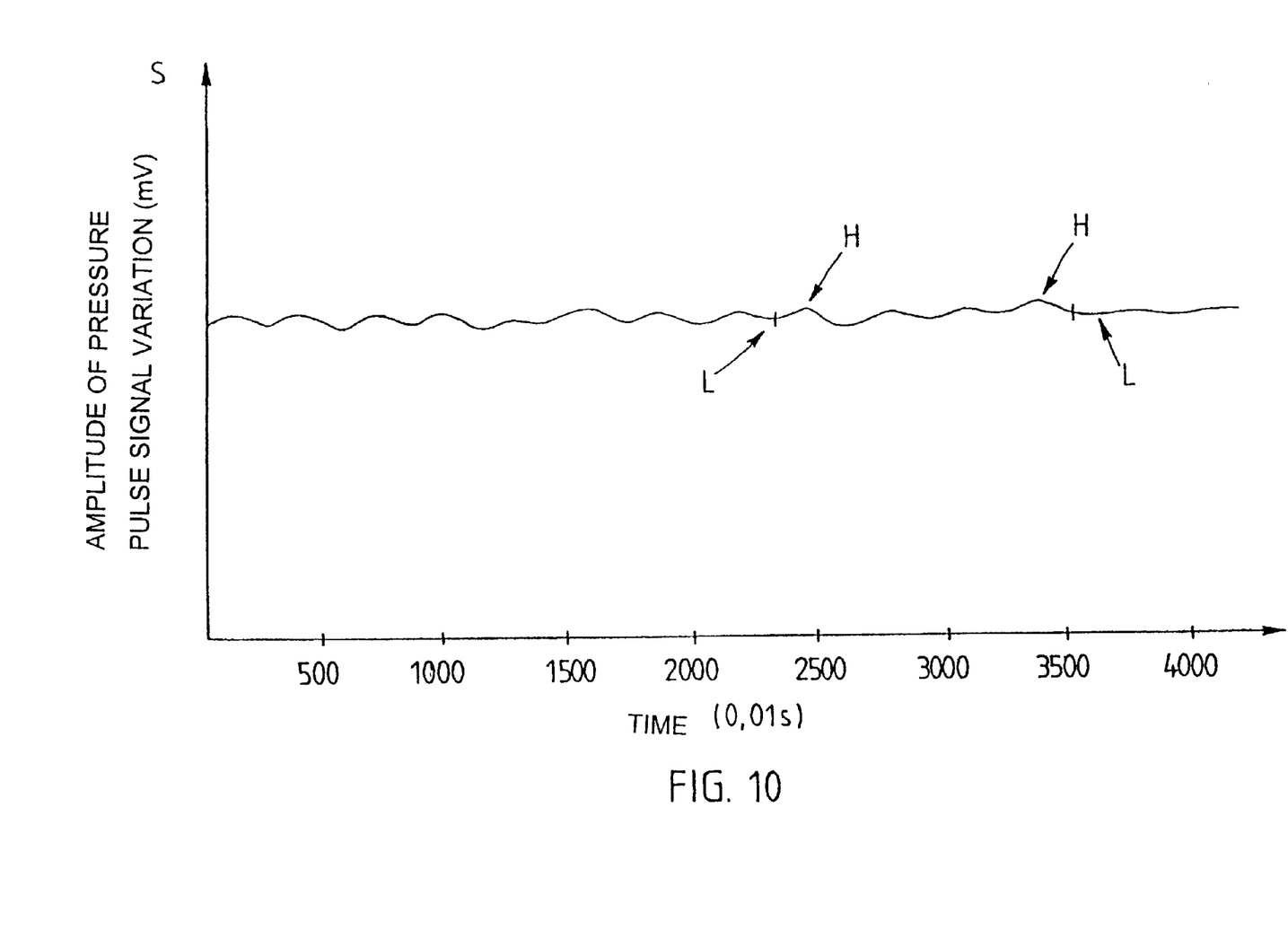
FIG. 10 shows a pressure pulse variation signal generated from the pressure pulse signal of FIG. 4.

FIG. 10 shows the above pressure pulse signal variation signal S, which can be implemented in various ways, of which five are described herein. Referring to FIGS. 4, 8 and 10, in an embodiment said upper and lower peaks are upper peaks H and lower peaks L of the variation signal S generated from the absolute maximums ABSMAX of the pressure pulse signal measured in the estimation. In a second version, said upper and lower peaks are upper peaks H and lower peaks L of the variation signal S generated from the absolute minimums ABSMIN of the pressure pulse signal measured in the estimation. In a third version said upper and lower peaks are upper peaks H and lower peaks L of the variation signal S generated from the local maximums LMAX of the pressure pulse signal measured in the estimation. In a fourth version said upper and lower peaks are upper peaks H and lower peaks L of the variation signal S generated from the local minimums LMIN of the pressure pulse signal measured in the estimation. In a fifth preferred version, said upper and lower peaks are upper peaks H and lower peaks L of a pressure pulse variation signal S to be generated from desired combinations of the absolute maximums ABSMAX, absolute minimums ABSMIN, local maximums LMAX, local minimums LMIN of the pressure pulse signal or other corresponding signal points. The combination may include two or more signal points, and the combination operation may be e.g. subtraction.

The above procedures help to clarify whether systolic and/or diastolic pressure has been measured at the maximum or minimum of the pressure pulse signal or somewhere between them. By means of this information a more accurate and correct range of variation can be given to the actual blood pressure measurement result.

The interpreting unit 9, particularly its core part, i.e. the interpreting element 9a, can be implemented by a programmable processor. The functions of the interpreting unit, e.g. the estimation functions performed by blocks 961 to 965 of the estimation block 960, can be implemented as program blocks of the interpreting unit, i.e. in practice the interpreting element.

As shown in FIGS. 1 and 3, in the measurement arrangement the estimation means 960 to 965 are preferably part of the wristband-type unit which further comprises said sensor 7 or 700 measuring the pressure pulse for the estimation.

In other words, the sensor 7 can be the same as is used in the actual blood pressure measurement. According to FIGS. 1 and 3, in the measurement arrangement the interpreting unit 9 is also preferably part of the wristband-type unit, or the interpreting unit forms a wristband-type unit 9, which in FIG. 1 comprises a pressure pulse sensor 7 for measuring the artery. This makes the measurement arrangement well integrated and compact.

Referring to FIGS. 1 and 3, in an embodiment the estimation means is part of a wristband-type or other type of unit, which is in a wireless connection 22, 32 or in a wired connection 21, 31 with said sensor 7 or 700 measuring the pressure pulse from the body for the estimation.

Figure 2:
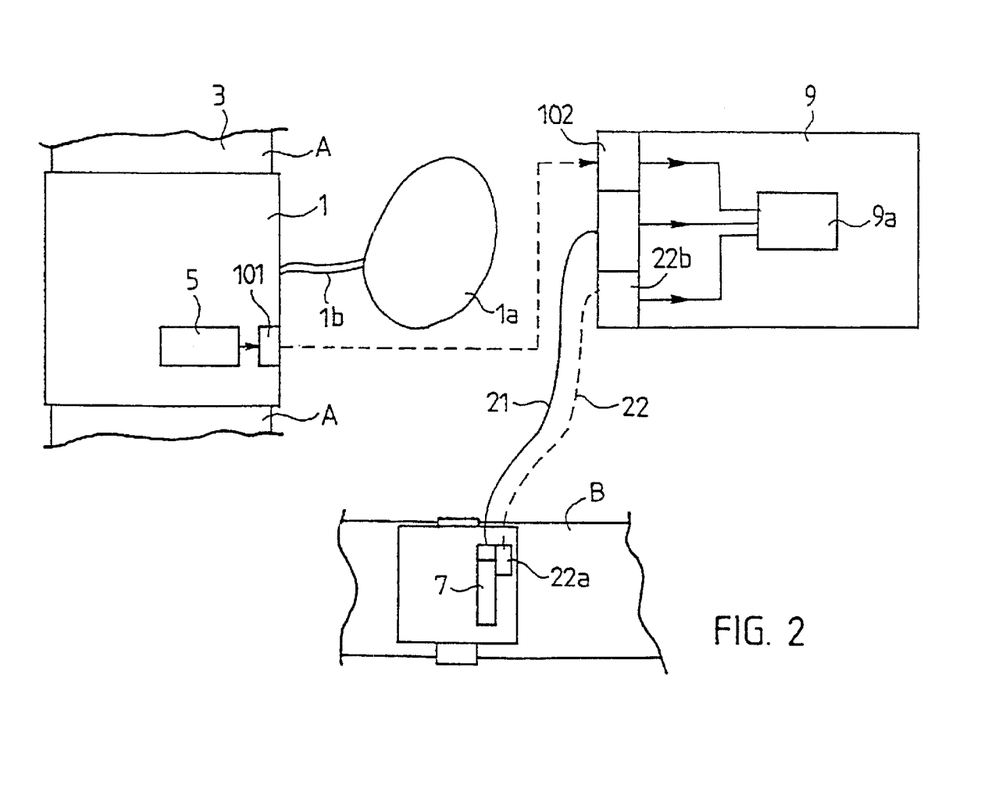
FIG. 2 shows a second embodiment of the measurement arrangement.

Referring to FIG. 2, an alternative solution can involve a separate interpreting unit 9, implemented by e.g. a microcomputer/measuring device or the like, the sensor 7 measuring the pressure pulse signal being in a wired connection 21 or in a wireless connection 22 with said interpreting unit 9. The wired connection 21 could be e.g. a cable 21 between the sensor 7 and the interpreting unit 9, i.e. a computer/measuring device provided with e.g. a measuring card. In FIG. 2, a dashed line 22 denotes a wireless connection between the arterial pressure pulse sensor 7 and the interpreting unit 9. The wireless connection 22 is preferably implemented by a magnetic inductive coupling 22a, 22b, comprising a transmitter element 22a controlled by the sensor 7 and comprising a coil, and a receiver element 22b disposed in the interpreting unit 9 and comprising a second coil.

A combination of the previous versions, i.e. a third embodiment in accordance with FIG. 3, is also feasible, i.e. the interpreting unit 9 and the estimation means 960 to 965 are a wristband-type unit, but in FIG. 3 the pressure pulse sensor 7 is not integrated with the interpreting unit 9, but is in a wired connection 31 or a wireless connection 32 with the interpreting unit 9. The connections 31, 32 can be implemented in the same way as was presented for the version of FIG. 2, i.e. by a cable 31 or as a magnetic inductive coupling 32. Reference numerals 32a, 32b denote the transmitter element 32a and receiver element 32b of the wireless telemetric magnetic inductive coupling.

In a preferred embodiment of the invention the pressure pulse sensor 7 is a multichannel sensor, most preferably a line sensor, i.e. an array sensor. In this case the pressure pulse is measured as a multichannel measurement. The different channels 7a to 7d of the multichannel line sensor 7 are shown in FIG. 1 in a simplified form. This provides a more reliable measurement result than with a mere single-channel sensor. In a preferred embodiment, the pressure pulse is measured in the radial artery area, where the arterial pressure pulse is easily detectable, and which is an easy point from the point of view of the subject of the measurement.

The pressure pulse does not necessarily have to be measured at the same point in the actual blood pressure measurement and in the estimation of the actual blood pressure measurement, but the applicant has found that it is simplest to make the measurements at the same point, since in that case the common sensor 7 does not have to be moved to a new location, and, on the other hand, two different sensors are not needed if moving is to be avoided.

In accordance with FIG. 6, in a preferred embodiment the measurement arrangement comprises an amplifier 110 and a filter 111 for amplifying and filtering the pressure pulse signal measured by the sensor 7, and an A/D converter 112 for performing AND conversion after filtering. The amplifier 110 can be e.g. a voltage or charging amplifier. The filter 111, in turn, is preferably a band-pass filter whose passband is e.g. within the range 1 to 10 Hz. If the estimation measurement and the actual blood pressure measurement share a common sensor 7, then the same components 110 to 112 can be used for processing the pressure pulse signal. Similarly, if the estimation measurement to be performed before or after the actual blood pressure measurement has a special second pressure pulse sensor 700, then the same components 110 to 112 can be used for processing the signal measured thereby as are used for the sensor 7 used in the actual blood pressure measurement. However, in a preferred embodiment of the invention, the same pressure pulse sensor 7 is used for the estimation measurement and the actual measurement.

In the estimation measurement and in the actual measurement the method is preferably such that the pressure pulse signal measured by the sensor 7 is amplified by the amplifier 110 and filtered by the filter 111, and then A/D converted by the converter 112. The amplification and filtering serve to eliminate interference and distortion, resulting in a sufficiently strong signal. The A/D conversion, in turn, converts the measured signal into a form which the interpreting unit 9 is able to interpret and process. FIGS. 2, 5 and 7 show the interpreting element 9a, e.g. a microprocessor, comprised by the interpreting unit 9. The versions shown by the other figures also comprise a similar component.

In fact, FIG. 7 shows the inner structure of the interpreting element 9a comprised by the interpreting unit 9. In FIG. 7, the interpreting element 9a comprises a part 901 for identifying the active pressure measurement signal, a part 902 for identifying the pressure pulse signal, a signal check part 903 connected to parts 901 and 902, a straight line fitting part 904 connected to part 903 and a SYS/DIAS determining part 905 connected to part 904. The SYS/DIAS determining part 905 determines the values of systolic and/or diastolic pressure according to what the straight line fitting algorithm (least squares principle) in the straight line fitting part 903 indicates on the basis of the received pressure measuring signal and pressure pulse signal. The straight line fitting algorithm serves to convert a discrete measurement into a form with continuous values.

As regards the invention, i.e. estimation of the accuracy of blood pressure measurement, the essential features include said blocks 960 to 965, i.e. the estimation means 960 and the associated means 961 to 965.

Referring to FIG. 7, in a preferred embodiment the interpreting unit 9 comprises, or at least has a connection to, a memory 906 and a display 907. The memory 906 and the display 907 can be external parts with respect to the interpreting element 9a, belonging or being connectable, however, to the interpreting unit 9. In a preferred embodiment the display 907 comprised by the measurement arrangement is common both for displaying the result of the estimation of the quality of the actual blood pressure measurement and for displaying the result of the actual blood pressure measurement. Such integration results in more readable measurements and is technically simpler.

Figure 9:
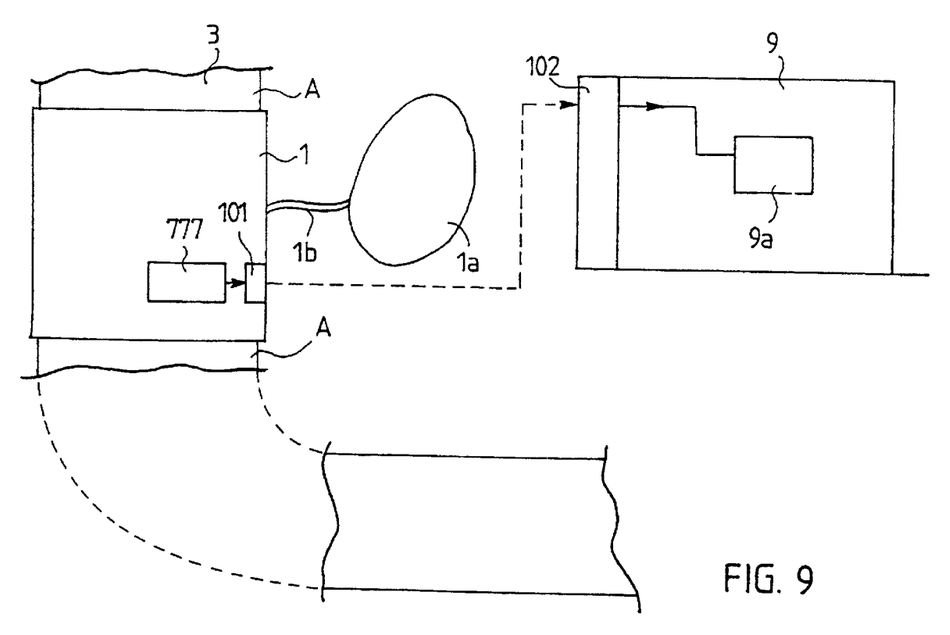
FIG. 9 shows an oscillometric type of device application, i.e. the second embodiment of the invention.

The invention is consequently suitable for a palpation method using a pressure pulse sensor 7 measuring the artery, but the device structure shown in FIG. 9 is suitable for an oscillometric measuring principle. FIG. 9 shows a measurement arrangement comprising a subject 3 to be measured, a cuff-like pressure generator 1 with a pump 1a, a sensor 777 and an interpreting means 9, 9a, i.e. the interpreting unit 9, 9a. The sensor 777 measures what is known as cuff pressure, i.e. a cuff pressure oscillation signal. In FIG. 9 the sensor 777 is in connection with the interpreting means 9, 9a, i.e. the interpreting unit, or observation means, by the means 101, 102. The connection 101, 102 can be wireless as in FIG. 9, or wired. In the method according to FIG. 9, a variable compressive acting pressure is applied at a compression point A to the measuring point, such as a person's extremity or the like, by a pressure generator, i.e. the pressure cuff 1, e.g. by immediately increasing the pressure to a high level and letting it change, i.e. decline, during the measurement. The method further involves determination of diastolic and/or systolic pressure by oscillometric blood pressure measurement to determine the measurement result of the actual blood pressure measurement by measuring by the sensor 777 a pressure oscillation signal measurable from the pressure generator. From said signal the interpreting means 9, 9a is able to determine the presence of an AC signal, and, consequently, systolic and diastolic pressure. The amplitude of the AC signal of what is known as the cuff pressure in the pressure generator, i.e. the cuff, increases to a certain point when pressure is reduced, whereupon the oscillation declines. As pressure falls, oscillation, i.e. AC-formed pressure oscillation signal, or amplitude variation, can be observed in the cuff pressure at the systolic pressure in block 9, 9a. In the oscillometric version shown by FIG. 9, the acting pressure is obtained from the DC portion of the signal measured by the measuring element 777. The effect of the acting pressure is obtained from an AC portion "on top of" the DC portion of the signal measured by the measuring element.

In addition to actual blood pressure measurement, the method according to FIG. 9 involves an estimation cycle for the actual measurement, during which the magnitude of the pressure oscillation signal is measured by the sensor 777 measuring the pressure oscillation signal. In the estimation, one or more statistical parameters are calculated from the pressure oscillation signal measurement data by means of the interpreting means 9, 9a and the estimation means 960 to 961 contained therein to represent the magnitude of pressure oscillation signal variation for forecasting and/or depicting the quality of the actual blood pressure measurement. This embodiment also utilizes the estimation means 960 whose structure and functions can be identical to those described herein. Estimation can take place before and/or after the actual blood pressure measurement. As regards this second embodiment, reference is made to the description of the first embodiment.

The result of the estimation can be expressed as a ± percent deviation or a ± numerical value, e.g. as mercuric millimetres mm Hg.

The magnetic inductive coupling, such as the coupling 101, 102, described above in different contexts, is based on applying a current with varying magnitude to the coil of the transmitter element 101, the coil generating a magnetic field with varying magnitude, the field being received by a second coil, i.e. by the coil of the receiver element 102. A magnetic inductive coupling is useful in small portable devices owing to its low power consumption. An inductive coupling is particularly useful in wristband-type versions according to FIGS. 1 and 3.

The preferred embodiments of the invention described above and the other features of the method and measurement arrangement presented in greater detail highlight the advantages of the basic invention.

The above described different means can be implemented in manners considered optimal, e.g. by separate components, by processors implemented by software or other components implemented by software, or as a combination of said techniques, as a mixed technique, or in other manners available at each stage of technological progress.

Although the invention is described herein with reference to the examples in accordance with the accompanying drawings, it will be appreciated that the invention is not to be so limited, but can be modified in a variety of ways within the scope of the inventive idea disclosed in the appended claims.

What is claimed is:

1. A method for blood pressure measurement, the method comprising applying a variable compressive acting pressure to a measuring point, such as a person's extremity or the like, at a compression point by a pressure generator, and at the same time measuring the effect of the variable pressure on the artery at a second point located farther away from the heart, i.e. closer to the end point of peripheral circulation than the compression point to which the pressure is applied, wherein diastolic pressure (PDIAS) and/or systolic pressure (PSYS) is determined as a result of an actual blood pressure measurement, characterized in that in addition to the actual blood pressure measurement, the method comprises using an estimation cycle for the actual measurement, during which the magnitude of a pressure pulse is measured by a sensor measuring a pressure pulse signal, and that one or more statistical parameters are calculated from the pressure pulse measurement data to represent the magnitude of pressure pulse variation for forecasting and/or depicting the quality of the actual blood pressure measurement.

2. A method for blood pressure measurement, the method comprising applying a variable compressive acting pressure to a measuring point, such as a person's extremity or the like, at a compression point by a pressure generator, determining diastolic pressure (PDIAS) and/or systolic pressure (PSYS) oscillometrically to determine the measurement result of an actual blood pressure measurement by measuring a pressure oscillation signal which is measurable from the pressure generator, characterized in that in addition to the actual blood pressure measurement, the method comprises using an estimation cycle for the actual measurement, during which the magnitude of the pressure oscillation signal is measured by a sensor measuring the pressure oscillation signal, and that one or more statistical parameters are calculated from the pressure oscillation signal measurement data to represent the magnitude of pressure oscillation signal variation for forecasting and/or depicting the quality of the actual blood pressure measurement.

3. A method as claimed in claim 1, characterized in that the estimation cycle either precedes or succeeds the actual blood pressure measurement or both precedes and succeeds the actual blood pressure measurement.

4. A method as claimed in claim 1, characterized in that if the estimation result surpasses reference values set for the quality of the actual blood pressure measurement, the actual blood pressure measurement is initiated, or the result of a performed actual measurement is accepted as the final result of the actual blood pressure measurement.

5. A method as claimed in claim 1, characterized in that if the estimation result is worse than reference values set for the quality of the actual blood pressure measurement, the actual blood pressure measurement is not initiated, or the result of a performed actual measurement is not accepted as the final result of the actual blood pressure measurement.

6. A method as claimed in claim 1, characterized by calculating one or more statistical parameters from the estimation cycle measurements: maximum, minimum, magnitude of pressure pulse signal amplitude variation, standard deviation of pressure pulse signal amplitude variation, standard deviation and/or mean of the absolute maximums (ABSMAX) of the pressure pulse signal, standard deviation and/or mean of the absolute minimums (ABSMIN) of the pressure pulse signal, standard deviation and/or mean of the local maximums (LMAX) of the pressure pulse signal, standard deviation and/or mean of the local minimums (LMIN) of the pressure pulse signal.

7. A method as claimed in claim 6, characterized in that the magnitude of the person's normal blood pressure variation owing to physiological or other reasons is determined in the estimation by means of one or more calculated statistical parameters.

8. A method as claimed in claim 7, characterized in that the normal range of variation in the blood pressure is determined on the basis of the magnitude of the normal variation in the blood pressure.

9. A method as claimed in claim 1, characterized in that the result of the estimation cycle is shown on a display.

10. A method as claimed in claim 1, characterized in that the result of the estimation cycle is shown together with the result of the actual blood pressure measurement.

11. A method as claimed in claim 1, characterized in that the reliability of the measurement result of the actual blood pressure measurement is estimated in the estimation of the quality of the actual blood pressure measurement which is performed on the basis of the measurements of the estimation cycle.

12. A method as claimed in claim 1, characterized in that a measurement-specific range of reliability for the measurement result of the actual blood pressure measurement is generated as a result of the estimation of the quality of the actual blood pressure measurement.

13. A method as claimed in claim 1, characterized in that the accuracy of the measurement result of the actual blood pressure measurement is estimated in the estimation of the quality of the actual blood pressure measurement which is performed on the basis of the measurements of the estimation cycle.

14. A method as claimed in claim 13, characterized in that a range of error is formed as a result of the estimation of the accuracy of the measurement result of the actual blood pressure measurement.

15. A method as claimed in claim 1, characterized in that the discrete representativeness of the measurement is estimated on the basis of the measurements of the estimation cycle.

16. A method as claimed in claim 1, characterized in that in one or more estimation cycles, an estimate is made as to whether the blood pressure value shows a trend towards a higher or lower value in the estimation cycle or if the trend is essentially indicative of a stable blood pressure value.

17. A method as claimed in claim 16, characterized in that the estimate of the occurrence of the trend is made by comparing the measurement data of two or more estimation cycles.

18. A method as claimed in claim 1, characterized in that the pressure pulse to be measured in the estimation cycle and the effect of the variable acting pressure on the artery to be measured in the actual blood pressure measurement are both made in the same area, i.e. farther away from the heart, or closer to the end point of peripheral circulation than the compression point, to which the pressure is applied in the actual blood pressure measurement.

19. A method as claimed in claim 1, characterized in that the pressure pulse measurement in the estimation cycle and the measurement of the effect of the pressure in the actual blood pressure measurement, also performed as pressure pulse measurement, are made by the same sensor.

20. A method as claimed in claim 1, characterized in that in the estimation cycle the pressure pulse is measured in the area of the radial artery.

21. A method as claimed in claim 1, characterized in that in the estimation cycle the measurement is carried out for a period of at least 20 seconds.

22. A method as claimed in claim 1, characterized in that the pressure pulse is measured as a multichannel measurement.

23. A method as claimed in claim 1, characterized in that the pressure pulse signal measured by the pressure pulse measuring sensor is amplified and filtered, and then subjected to A/D conversion.

24. A method as claimed in claim 1, characterized by observing the pressure pulse signal measurement in the estimation cycle (EC) and the pressure pulse signal measurement in the actual blood pressure measurement cycle (MC) as comparable measurements with regard to time, and by determining the point where the instant of determining the diastolic pressure (PDIAS) in the actual blood pressure measurement is located in relation to upper and lower peaks of a pressure pulse signal variation signal (S) generated on the basis of the estimation cycle (EC) measurement.

25. A method as claimed in claim 1, characterized by observing the pressure pulse signal measurement of the estimation cycle (EC) and the pressure pulse signal measurement of the actual blood pressure measurement cycle (MC) as comparable measurements with respect to time, and by determining the point where the instant of determining the systolic pressure (PSYS) of the actual blood pressure measurement is located in relation to upper and lower peaks of a pressure pulse signal variation signal (S) estimated on the basis of the estimation cycle measurement (EC).

26. A method as claimed in claim 24, characterized in that said upper and lower peaks are upper and lower peaks of a variation signal (S) generated from the absolute maximums (ABSMAX) of the pressure pulse signal (S) measured in the estimation.

27. A method as claimed in claim 24, characterized in that said upper and lower peaks are upper and lower peaks of a variation signal (S) generated from the absolute minimums (ABSMIN) of the pressure pulse signal (S) measured in the estimation.

28. A method as claimed in claim 24, characterized in that said upper and lower peaks are upper and lower peaks of a variation signal (S) generated from the local maximums (LMAX) of the pressure pulse signal (S) measured in the estimation.

29. A method as claimed in claim 24, characterized in that said upper and lower peaks are upper and lower peaks of a variation signal (S) generated from the local minimums (LMIN) of the pressure pulse signal (S) measured in the estimation.

30. A method as claimed in claim 24, characterized in that said upper and lower peaks are upper and lower peaks of a variation signal (S) generated from desired combinations of the absolute maximums (ABSMAX), absolute minimums (ABSMIN), local maximums (LMAX), local minimums (LMIN) of the pressure pulse signal or other corresponding signal points.

31. An arrangement for blood pressure measurement, comprising:

a pressure generator for applying an acting pressure to a measuring point, such as a person's extremity or the like, a measuring element for measuring the acting pressure, an interpreting unit for determining systolic pressure (PSYS) and/or diastolic pressure (PDIAS), a sensor for simultaneous measurement of the effect of the variable pressure on an artery at a second point, said second point being farther away from the heart, i.e. closer to the end point of peripheral circulation, than the compression point to which the acting pressure is applied, and estimation means for estimating the quality of an actual blood pressure measurement, and that the estimation means is in connection with the sensor measuring the pressure pulse at the measuring point and feeding the measurement data to the estimation means, the sensor being either the same sensor that is used in the actual blood pressure measurement for measuring the effect of the acting pressure, or a second, different sensor, and that the estimation means further includes a calculation means, adapted to calculate from the measurement data measured by the pressure pulse sensor one or more statistical parameters representing the magnitude of pressure pulse variation for forecasting and/or depicting the quality of the actual blood pressure measurement.

32. An arrangement for blood pressure measurement, comprising:

a pressure generator for applying an acting pressure to a measuring point, such as a person's extremity or the like, a measuring element for measuring the acting pressure and its effect by measuring a pressure oscillation signal of the pressure generator, an interpreting unit for determining systolic pressure (PSYS) and/or diastolic pressure (PDIAS) oscillometrically from the pressure oscillation signal, and estimation means for estimating the quality of an actual blood pressure measurement, and that the estimation means is in connection with the measuring element or with a sensor measuring the pressure oscillation signal and feeding the measurement data to the estimation means, and that the estimation means further includes a calculation means, adapted to calculate from the measurement data of the measured pressure oscillation signal one or more statistical parameters representing the magnitude of pressure oscillation signal variation for forecasting and/or depicting the quality of the actual blood pressure measurement.

33. A measurement arrangement as claimed in claim 31, characterized in that for estimating the blood pressure measurement, a measurement is performed before or after the actual blood pressure measurement, or both before and after the actual blood pressure measurement.

34. A measurement arrangment as claimed in claim 31, characterized in that the estimation means comprises a reference comparator, arranged to compare the result of the estimation with reference values set for the quality of the actual blood pressure measurement, and that if the estimation result surpasses the reference values set for the quality of the actual blood pressure measurement, the actual blood pressure measurement is initiated, controlled by the reference comparator, or the mesurement result of a performed actual blood pressure measurement is accepted as the final result.

35. A measurement arrangement as claimed in claim 31, characterized in that the estimation means comprises a reference comparator, arranged to compare the result of the estimation with reference values set for the quality of the actual blood pressure measurement, and that if the estimation result is worse than the reference values set for the quality of the actual blood pressure measurement, the actual blood pressure measurement is not initiated or the measurement result of a performed actual blood pressure measurement is rejected.

36. An arrangement as claimed in claim 31, characterized in that the calculation means is arranged to calculate one or more of the following statistical parameters: magnitude of pressure pulse signal amplitude variation, standard deviation of pressure pulse signal amplitude variation, standard deviation and/or mean of the absolute maximums (ABSMAX) of the pressure pulse signal, standard deviation and/or mean of the absolute minimums (ABSMIN) of the pressure pulse signal, standard deviation and/or mean of the local maximums (LMAX) of the pressure pulse signal, standard deviation and/or mean of the local minimums (LMIN) of the pressure pulse signal.

37. An arrangement as claimed in claim 31, characterized in that the estimation means comprises a trend indicator, arranged to estimate if the blood pressure value shows a trend towards a higher or lower value during estimation or if the trend is essentially indicative of a stable blood pressure value.

38. An arrangement as claimed in claim 31, characterized in that the pressure pulse measuring sensor or the pressure oscillation signal measuring element is a multichannel sensor.

39. An arrangement as claimed in claim 31, characterized by comprising a display for displaying the result of the estimation.

40. An arrangement as claimed in claim 39, characterized in that the display is common both for displaying the result of the estimation of the quality of the actual blood pressure measurement and for displaying the result of the actual blood pressure measurement.

41. An arrangement as claimed in claim 31, characterized in that the arrangement comprises an amplifier and filter for amplifying and filtering the pressure pulse signal measured by the sensor, and and A/D converter for performing A/D conversion after filtering.

42. An arrangement as claimed in claim 31, characterized in that the estimate means is part of a wristband type of unit, which also comprises the pressure pulse measuring sensor for said estimation.

43. An arrangement as claimed in claim 31, characterized in that the estimation means is part of a wristband type or other type of unit, which is in a wireless connection or in a wired connection with said sensor measuring the pressure pulse from the body for the estimation.

44. An arrangement as claimed in claim 31, characterized in that the estimation means is part of the same entity as the interpreting unit.

45. An arrangement as claimed in claim 44, characterized in that the estimation means is part of the interpreting unit.

46. An arrangement as claimed in claim 31, characterized in that the estimation means comprises a means for observing the pressure pulse signal measurement in the estimation cycle (EC) and the pressure pulse signal measurement in the actual blood pressure measurement cycle (MC) as comparable measurements with regard to time, and a determination means for determining the point where the instant of determining the diastolic pressure (PDIAS) in the actual blood pressure measurement is located in relation to upper and lower peaks of a pressure pulse signal variation signal (S) generated on the basis of the estimation cycle measurement (EC).

47. An arrangement as claimed in claim 31, characterized in that the estimation means comprises a means for observing the pressure pulse signal measurement in the estimation cycle (EC) and the pressure pulse signal measurement in the actual blood pressure measurement cycle (MC) as comparable measurements with regard to time, and a determination means for determining the point where the instant of determining the systolic pressure (PSYS) in the actual blood pressure measurement is located in relation to upper and lower peaks of a pressure pulse signal variation signal (S) according to the trend estimated on the basis of the estimation cycle measurement (EC).

48. An arrangement as claimed in claim 31, characterized in that the sensor employed in the actual blood pressure measurement for measuring the effect of the acting pressure at the second point is a sensor which measures the effect of the acting pressure and the pressure pulse generated by heartbeat and is coupled to said interpreting unit, to which a measuring signal indicative of the measurement value of the acting pressure is also coupled, and that said interpreting unit is arranged to determine diastolic pressure (PDIAS) and/or systolic pressure (PSYS) on the basis of a pressure which is acting upon the detection of a change, characteristic of diastolic pressure (PDIAS) and/or systolic pressure (PSYS), in the pressure pulse signal measured by the sensor.

49. A method for blood pressure measurement, the method comprising applying a variable compressive acting pressure to a measuring point, such as a person's extremity or the like, at a compression point by a pressure generator, and at the same time measuring the effect of the variable pressure on the artery at a second point located farther away from the heart, i.e. closer to the end point of peripheral circulation than the compression point to which the pressure is applied, wherein diastolic pressure (PDIAS) and/or systolic pressure (PSYS) is determined as a result of an actual blood pressure measurement, characterized in that in addition to the actual blood pressure measurement, the method comprises using an estimation cycle for the actual measurement, during which the magnitude of a pressure pulse is measured by a sensor measuring a pressure pulse signal, wherein the pressure pulse is measured in the area of the radial artery, and that one or more statistical parameters are calculated from the pressure pulse measurement data to represent the magnitude of pressure pulse variation for forecasting and/or depicting the quality of the actual blood pressure measurement.

50. A method for blood pressure measurement, the method comprising applying a variable compressive acting pressure to a measuring point, such as a person's extremity or the like, at a compression point by a pressure generator, and at the same time measuring the effect of the variable pressure on the artery at a second point located farther away from the heart, i.e. closer to the end point of peripheral circulation than the compression point to which the pressure is applied, wherein diastolic pressure (PDIAS) and/or systolic pressure (PSYS) is determined as a result of an actual blood pressure measurement, characterized in that in addition to the actual blood pressure measurement, the method comprises using an estimation cycle for the actual measurement, during which the magnitude of a pressure pulse is measured by a sensor measuring a pressure pulse signal, wherein the pressure pulse is measured as a multichannel measurement, and that one or more statistical parameters are calculated from the pressure pulse measurement data to represent the magnitude of pressure pulse variation for forecasting and/or depicting the quality of the actual blood pressure measurement.

51. An arrangement for blood pressure measurement, comprising:

a pressure generator for applying an acting pressure to a measuring point, such as a person's extremity or the like, a measuring element for measuring the acting pressure, an interpreting unit for determining systolic pressure (PSYS) and/or diastolic pressure (PDIAS), a sensor for simultaneous measurement of the effect of the variable pressure on an artery at a second point, said second point being farther away from the heart, i.e. closer to the end point of peripheral circulation, than the compression point to which the acting pressure is applied, wherein said sensor is a multichannel sensor, an estimation means for estimating the quality of an actual blood pressure measurement, and that the estimation means is in connection with the sensor measuring the pressure pulse at the measuring point and feeding the measurement data to the estimation means, the sensor being either the same sensor that is used in the actual blood pressure measurement for measuring the effect of the acting pressure, or a second, different sensor, and that the estimation means further includes a calculation means, adapted to calculate from the measurement data measured by said sensor one or more statistical parameters representing the magnitude of pressure pulse variation for forecasting and/or depicting the quality of the actual blood pressure measurement.

52. An arrangement for blood pressure measurement, comprising:

a pressure generator for applying an acting pressure to a measuring point, such as a person's extremity or the like, a measuring element for measuring the acting pressure, an interpreting unit for determining systolic pressure (PSYS) and/or diastolic pressure (PDIAS), a sensor for simultaneous measurement of the effect of the variable pressure on an artery at a second point, said second point being farther away from the heart, i.e. closer to the end point of peripheral circulation, than the compression point to which the acting pressure is applied, an estimation means for estimating the quality of an actual blood pressure measurement, and that the estimation means is in connection with the sensor measuring the pressure pulse at the measuring point and feeding the measurement data to the estimation means, the sensor being either the same sensor that is used in the actual blood pressure measurement for measuring the effect of the acting pressure, or a second, different sensor, and that the estimation means further includes a calculation means, adapted to calculate from the measurement data measured by said sensor one or more statistical parameters representing the magnitude of pressure pulse variation for forecasting and/or depicting the quality of the actual blood pressure measurement, and said estimation means is part of a wrist band type of unit, which also includes said sensor for said estimation.

53. An arrangement for blood pressure measurement, comprising:

a pressure generator for applying an acting pressure to a measuring point, such as a person's extremity or the like, a measuring element for measuring the acting pressure, an interpreting unit for determining systolic pressure (PSYS) and/or diastolic pressure (PDIAS), a sensor for simultaneous measurement of the effect of the variable pressure on an artery at a second point, said second point being farther away from the heart, i.e. closer to the end point of peripheral circulation, than the compression point to which the acting pressure is applied, an estimation means for estimating the quality of an actual blood pressure measurement, and that the estimation means is in connection with the sensor measuring the pressure pulse at the measuring point and feeding the measurement data to the estimation means, the sensor being either the same sensor that is used in the actual blood pressure measurement for measuring the effect of the acting pressure, or a second, different sensor, and that the estimation means further includes a calculation means, adapted to calculate from the measurement data measured by said sensor one or more statistical parameters representing the magnitude of pressure pulse variation for forecasting and/or depicting the quality of the actual blood pressure measurement, and said estimation means is part of a wrist band type or other type of unit, which is in a wireless connection or in a wired connection with said sensor measuring the pressure pulse from the body for the estimation.

* * * * *

UNITED STATES PATENT AND TRADEMARK OFFICE
CERTIFICATE OF CORRECTION

PATENT NO. : 6,443,905 B1
DATED : September 3, 2002
INVENTOR(S) : Nissila et al.

It is certified that error appears in the above-identified patent and that said Letters Patent is hereby corrected as shown below:

Column 5,
Line 42, now reads "pressure sure", should read -- pressure --.

Column 11,
Line 22, now reads "and conversion", should read -- A/D conversion --.

Column 15,
Lines 26-28 and lines 32-34, delete claims 20 and 22

Column 17,
Lines 47-50 and lines 64-67, delete claims 38 and 42

Column 18,
Lines 1-5, delete claim 43

Signed and Sealed this

Eleventh Day of February, 2003

JAMES E. ROGAN
*Director of the United States Patent and Trademark Office*